US00PP14741P3

(12) United States Plant Patent
Danziger

(10) Patent No.: US PP14,741 P3
(45) Date of Patent: Apr. 27, 2004

(54) IMPATIENS PLANT NAMED 'DANCHESAL'

(50) Latin Name: *Impatiens walleriana*
Varietal Denomination: Danchesal

(75) Inventor: Gabriel Danziger, Nir-Zvi (IL)

(73) Assignee: Danziger "DAN" Flower Farm (IL)

( * ) Notice: Subject to any disclaimer, the term of this patent is extended or adjusted under 35 U.S.C. 154(b) by 0 days.

(21) Appl. No.: 10/230,303

(22) Filed: Aug. 29, 2002

(65) Prior Publication Data

US 2004/0045066 P1 Mar. 4, 2004

(51) Int. Cl.[7] ..... A01H 5/00

(52) U.S. Cl. ..... Plt./317

(58) Field of Search ..... Plt./317

*Primary Examiner*—Bruce R. Campell
*Assistant Examiner*—June Hwu
(74) *Attorney, Agent, or Firm*—Foley & Lardner

(57) ABSTRACT

A new and distinct Impatiens plant named 'Danchesal' characterized by having compact growth habit; small flowers; small, green leaves; and salmon color flowers.

1 Drawing Sheet

Latin name of the genus and species of the plant claimed: *Impatiens walleriana.*
Variety denomination: Danchesal.

BACKGROUND OF THE INVENTION

The present invention relates to a new and distinct cultivar of Impatiens plant, botanically known as *Impatiens walleriana*, hereinafter referred to by the cultivar name 'Danchesal'.

The new cultivar originated from a cross made in a controlled breeding program in Moshav Mishmar Hashiva, Israel. The female parent is RRB-401 (unpatented, proprietary variety). The male parent is BGA-800 (unpatented, proprietary variety). 'Danchesal' was discovered and selected by the inventor, Gabriel Danziger, as a flowering plant within the progeny of the stated cross in a controlled environment in Moshav Mishmar Hashiva, Israel.

Asexual reproduction of the new cultivar by leaves cutting was first performed in April, 1999 in Moshav Mishmar Hashiva, Israel and has demonstrated that the combination of characteristics as herein disclosed for the new cultivar are firmly fixed and retained through successive generations of asexual reproduction. The new cultivar reproduces true-to-type.

BRIEF SUMMARY OF THE INVENTION

The following traits have been repeatedly observed and are determined to be basic characteristics of 'Danchesal' which in combination distinguish this Impatiens as a new and distinct cultivar:

1. compact growth habit;
2. small flowers;
3. small, green leaves; and
4. salmon color flowers.

'Danchesal' has not been observed under all possible environmental conditions. The phenotype of the new cultivar may vary significantly with variations in environment such as temperature, light intensity, and daylength without any change in the genotype of the plant.

Of the many commercial cultivars known to the inventor, the most similar in comparison to 'Danchesal' is the Impatiens variety 'Fify Orange' (U.S. Plant Pat. No. 11,430), commercially known as 'Firefly Orange'.

TABLE 1

| | 'Danchesal' | 'Firefly Orange' |
|---|---|---|
| Flower Color-upper surface | RHS 40D | RHS 32A |
| Leaves Color-upper surface | RHS 137C | RHS 137C |
| Flower Size | 2.5 cm | 2.4 cm |

BRIEF DESCRIPTION OF THE DRAWING

The accompanying photographic drawings illustrate the overall appearance of the new Impatiens showing the colors as true as is reasonably possible with colored reproductions of this type. The drawing shows a whole plant side-view of a flowering 'Danchesal' plant.

DETAILED BOTANICAL DESCRIPTION

The following observations, measurements and values describe the new cultivar as grown in Moshav Mishmar Hashiva, Israel under conditions which closely approximate those generally used in commercial practice. The plant was grown in a greenhouse under the typical weather conditions in Israel (Winter night time temperature 18° C., winter day time temperature 20–25° C.; summer night time temperature approximately 25° C., summer day time temperature approximately 30° C.). Fertilization: N: P: K=5:3:8, N=100 ppm.

Color references are made to The Royal Horticultural Society Colour Chart (R.H.S.), except where general colors of ordinary significance are used. Color values were taken under daylight conditions at approximately noon in Moshav Mishmar Hashiva, Israel. The age of the plant described is 13 weeks from planting. The plant was asexually reproduced by leaf cuttings.

Plant:

*General appearance and form.*—Height: 14 cm. Plant spread: Compact, 30 cm. Lateral branches: Length—13 cm; internode length approximately 2 cm; diameter 0.5 cm; branch color RHS 143C; anthocyanin color RHS 184B. Flowering Response: Flowers at any day length. Flowering Season: Year round as grown in a greenhouse with winter night time temperature of 18° C., winter day time temperature of 20–25° C.; summer night time temperature of approximately 25° C., and summer day time temperature of approximately 30° C. Winter Hardiness: Resistance to 10° C. Lastingness of the Individual Bloom: About 15 days. Rooting Habit Description: Adventitious roots from cutting base. Time to initiate roots: 10 days. Time to produce a rooted cutting or liner: 17 days. Growth and branching habit: Compact growth habit; strong branching. Crop time: 10 weeks after planting as a 10–12 cm pot. Fragrance: None.

Foliage:

*Leaf Shape.*—Elliptic.

*Apex.*—Acuminate.

*Base.*—Acute.

*Length.*—Approximately 3 cm.

*Width.*—Approximately 2 cm.

*Margin.*—Shallowly serrate.

*Texture.*—Smooth.

*Color of upper surface.*—Mature leaf: RHS 137C. Immature leaf: RHS 137A.

*Color of lower surface.*—Mature leaf: RHS 143D. Immature leaf: RHS 143D.

*Venation.*—Pinnate.

*Petiole.*—Length: 1.5 cm. Diameter: 1 mm. Color: RHS 144D.

Inflorescence:

*Flower type and habit.*—Single flower, day neutral.

*Overall shape.*—Irregular — 5 petaled.

*Flower size.*—Diameter 2.5 cm.

*Average number of flowers per lateral branch.*—Approximately 14.

*Petals.*—Petal Number: 5. Petal Shape: Irregular — 5 petaled; apex obtuse; base acute; margin entire. Texture: Smooth. Petal size: Length approximately 1.3 cm; width approximately 1 cm. Petal Color: Upper surface: Salmon RHS 40D, reddish-purple towards the base RHS 61B. Lower surface: RHS 41C.

*Sepals.*—Number: 2. Shape: Elliptic. Length: 2 mm. Width: 1 mm. Apex: Acute. Margin: Entire. Color: Yellow-green, RHS 144C.

*Stem.*—Average length: 14 cm. Average diameter: 1 cm. Color: RHS 143C. Internode length: Approximately 1.5–2 cm.

*Spur.*—Length 2.5 cm; color light salmon-orange RHS 26C.

*Bud.*—Rate of opening: From the emergence of color until anthesis: 2 days. Color: RHS 12D. Shape: Conical. Length: 0.7 cm. Diameter: 0.4 cm.

*Peduncles.*—Length about 2.2 cm; slightly upward angle; stable strength surface texture; color yellow-green, RHS 144B.

Reproductive organs:

*Stamen.*—Size: 2 mm. Number: 5. Color: Purple RHS 77C.

*Seeds.*—Width: 1 mm. Length: 1 mm. Shape: Lanceolate. Color: Brown RHS 165A.

*Fruit.*—Size: 0.5 mm. Color: Green RHS 144A. Anthers: Color: RHS 63B.

*Pollen.*—None.

*Pistil.*—Size: 2 mm.

*Stigma.*—Color: Green RHS 144B.

*Ovary.*—Color: Green RHS 144B.

Disease resistance: No sensitivity to disease was observed under regular growing conditions.

I claim:

1. A new and distinct Impatiens plant named 'Danchesal', substantially as illustrated and described herein.

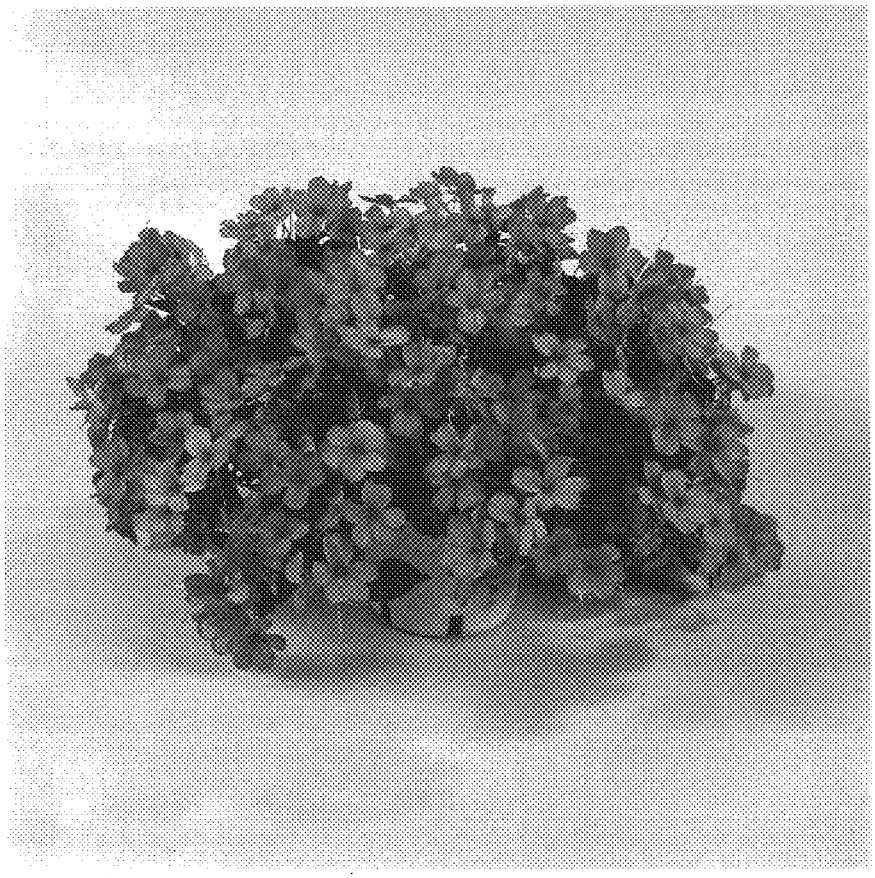

* * * * *